United States Patent
Nozawa et al.

(10) Patent No.: US 10,765,388 B2
(45) Date of Patent: Sep. 8, 2020

(54) RADIATION-IRRADIATION DEVICE COMPRISING A FIRST ARM, A SECOND ARM, AND MAIN BODY SURFACE REGULATING A ROTATIONAL MOVEMENT OF THE SECOND ARM

(71) Applicant: FUJIFILM Corporation, Tokyo (JP)

(72) Inventors: Yasuhisa Nozawa, Kanagawa (JP); Noriyuki Onobori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 240 days.

(21) Appl. No.: 15/865,544

(22) Filed: Jan. 9, 2018

(65) Prior Publication Data

US 2018/0146940 A1 May 31, 2018

Related U.S. Application Data

(63) Continuation of application No. PCT/JP2016/003454, filed on Jul. 26, 2016.

(30) Foreign Application Priority Data

Jul. 27, 2015 (JP) ................................. 2015-147524

(51) Int. Cl.
*A61B 6/00* (2006.01)
*A61B 6/10* (2006.01)

(52) U.S. Cl.
CPC .............. *A61B 6/4458* (2013.01); *A61B 6/00* (2013.01); *A61B 6/10* (2013.01); *A61B 6/102* (2013.01);
(Continued)

(58) Field of Classification Search
CPC ........... A61B 6/10; A61B 6/102; A61B 6/105; A61B 6/42; A61B 6/4208; A61B 6/4283;
(Continued)

(56) References Cited

U.S. PATENT DOCUMENTS 3,801,790 A * 4/1974 Götzl .................... A61B 6/105
378/198
6,193,415 B1 * 2/2001 Kadowaki ........... A61B 6/4405
378/197
(Continued)

FOREIGN PATENT DOCUMENTS

CN        201019755 Y      2/2008
CN        104068879 A     10/2014
(Continued)

OTHER PUBLICATIONS

Toshiba Medical Supply Co., Ltd., X-ray equipment IPF-21, [online], [Search on Apr. 3, 2015], Internet <URL:http://www.toshiba-medical.co.jp/tmd/products/xray/mobile/ipf21/index.html>, 4 pages.
(Continued)

*Primary Examiner* — Allen C. Ho
(74) *Attorney, Agent, or Firm* — Sughrue Mion, PLLC

(57) ABSTRACT

A radiation-irradiation device includes a leg unit, a radiation source unit, an arm unit, a body unit, and a raising/lowering mechanism. The arm unit includes a first arm connected to the radiation source unit, a second arm, a first rotational moving portion that connects the first arm to the second arm so as to allow the first arm and second arm to be rotationally movable relative to each other, and a second rotational moving portion that connects the second arm to the raising/lowering mechanism so as to allow the second arm to be rotationally movable relative to the raising/lowering mechanism. The rotation of the second arm from an initial rotational movement position is regulated by the body unit in a case in which the arm unit is positioned at a position other than a first position where the arm unit is raised or lowered by the raising/lowering mechanism.

10 Claims, 11 Drawing Sheets

(52) U.S. Cl.
CPC ............... *A61B 6/105* (2013.01); *A61B 6/42* (2013.01); *A61B 6/4208* (2013.01); *A61B 6/4283* (2013.01); *A61B 6/44* (2013.01); *A61B 6/4405* (2013.01); *A61B 6/4411* (2013.01); *A61B 6/4429* (2013.01); *A61B 6/4452* (2013.01); *A61B 6/46* (2013.01); *A61B 6/461* (2013.01); *A61B 6/462* (2013.01); *A61B 6/54* (2013.01); *A61B 6/40* (2013.01)

(58) Field of Classification Search
CPC ....... A61B 6/44; A61B 6/4405; A61B 6/4411; A61B 6/4429; A61B 6/4435; A61B 6/4441; A61B 6/4447; A61B 6/4452; A61B 6/40; A61B 6/4458; A61B 6/46; A61B 6/461; A61B 6/462
USPC .......................... 378/62, 98.8, 189, 196–198
See application file for complete search history.

(56) References Cited

U.S. PATENT DOCUMENTS

| | | | | |
|---|---|---|---|---|
| 6,237,707 B1 * | 5/2001 | Lyke | ................... | G05B 19/427 180/19.3 |
| 6,851,853 B2 * | 2/2005 | Nakagawa | ........... | A61B 6/4405 378/197 |
| 7,309,159 B2 * | 12/2007 | Watanabe | ................ | A61B 6/10 378/117 |
| 8,376,612 B2 * | 2/2013 | Takae | ................... | A61B 6/4283 378/198 |
| 8,419,276 B2 * | 4/2013 | Oda | ..................... | A61B 6/4283 378/198 |
| 8,568,028 B2 * | 10/2013 | Wendlandt | ............ | A61B 6/447 378/193 |
| 8,622,614 B2 * | 1/2014 | Carmichael | ......... | A61B 6/4266 378/198 |
| 8,708,561 B2 * | 4/2014 | Eaves | ................. | A61B 6/4233 378/198 |
| 8,721,176 B2 * | 5/2014 | McBroom | ............... | A61B 6/56 378/189 |
| 8,840,304 B2 * | 9/2014 | Perez Zarate | ........ | A61B 6/4405 378/197 |
| 8,899,834 B2 * | 12/2014 | Barker | ................ | A61B 6/4405 250/370.09 |
| 8,944,681 B2 * | 2/2015 | Soto | ..................... | A61B 6/4405 378/102 |
| 8,961,011 B2 * | 2/2015 | Lalena | ................ | A61B 6/4405 378/197 |
| 9,022,650 B2 * | 5/2015 | Kaku | ...................... | H05G 1/02 378/102 |
| 9,055,911 B2 * | 6/2015 | Sakuragi | .............. | A61B 6/4429 |
| 9,078,597 B2 * | 7/2015 | Patil | ...................... | A61B 6/107 |
| 9,084,582 B2 * | 7/2015 | Omura | ................ | A61B 6/4405 |
| 9,101,319 B2 * | 8/2015 | Kojima | ............... | A61B 6/4405 |
| 9,105,441 B2 * | 8/2015 | Matsuda | ................ | H01J 35/16 |
| 9,121,805 B2 * | 9/2015 | Omura | ................ | A61B 6/4405 |
| 9,125,611 B2 * | 9/2015 | Eaves | ................. | A61B 6/4405 |
| 9,173,628 B2 * | 11/2015 | Bouvier | ............. | A61B 6/4405 |
| 9,198,270 B2 * | 11/2015 | Chicchetti | ................ | H05G 1/08 |
| 9,275,770 B2 * | 3/2016 | Omura | ..................... | G21K 5/10 |
| 9,282,940 B2 * | 3/2016 | Nishimura | ........... | A61B 6/4405 |
| 9,295,438 B2 * | 3/2016 | Omura | ................. | A61B 6/4405 |
| 9,326,747 B2 * | 5/2016 | Omura | ................. | A61B 6/4405 |
| 9,413,961 B2 * | 8/2016 | Welsh | .................. | A61B 6/4405 |
| 9,414,795 B2 * | 8/2016 | Nakata | ................. | A61B 6/4429 |
| 9,414,802 B2 * | 8/2016 | Urbon | ................. | A61B 6/4283 |
| 9,456,799 B2 * | 10/2016 | Chicchetti | .............. | A61B 6/563 |
| 9,480,445 B2 * | 11/2016 | Guldstrand | .......... | A61B 6/4405 |
| 9,521,984 B2 * | 12/2016 | Moreno Vallejo | ... | A61B 6/4405 |
| 9,561,009 B2 * | 2/2017 | Woudstra | ............. | A61B 6/4405 |
| 9,561,013 B2 * | 2/2017 | Tsuchiya | .............. | A61B 6/4458 |
| 9,655,575 B2 * | 5/2017 | Park | ...................... | A61B 6/4233 |
| 9,655,582 B2 * | 5/2017 | Shirota | .................... | A61B 6/54 |
| 9,668,708 B2 * | 6/2017 | Okuno | ................... | A61B 6/447 |
| 9,693,437 B2 * | 6/2017 | Simmons | ............... | G01N 23/04 |
| 9,693,746 B2 * | 7/2017 | Ancar | ...................... | A61B 6/08 |
| 9,730,653 B2 * | 8/2017 | Niizeki | ................ | A61B 6/4405 |
| 9,788,810 B2 * | 10/2017 | Ancar | .................... | A61B 6/487 |
| 9,861,328 B2 * | 1/2018 | Kang | .................... | A61B 6/4452 |
| 9,883,841 B2 * | 2/2018 | Bååt | ...................... | A61B 6/4283 |
| 9,931,089 B2 * | 4/2018 | Nariyuki | ................ | A61B 6/107 |
| 9,949,702 B2 * | 4/2018 | Nam | ..................... | A61B 6/4291 |
| 10,022,105 B2 * | 7/2018 | Kudo | ..................... | A61B 6/563 |
| 10,058,303 B2 * | 8/2018 | Shimohira | ............ | A61B 6/06 |
| 10,064,588 B2 * | 9/2018 | Uchida | ................ | A61B 6/4405 |
| 10,076,293 B2 * | 9/2018 | Sehnert | ................... | A61B 6/06 |
| 10,219,764 B2 * | 3/2019 | Yang | .................... | A61B 6/4266 |
| 10,271,802 B2 * | 4/2019 | Wendlandt | ............. | A61B 6/105 |
| 10,278,654 B2 * | 5/2019 | Sadakane | ............... | A61B 6/025 |
| 10,292,673 B2 * | 5/2019 | Niizeki | ................. | A61B 6/547 |
| 10,433,805 B2 * | 10/2019 | Hishida | .................... | A61B 6/56 |
| 10,456,100 B2 * | 10/2019 | Ninomiya | ............ | A61B 6/4405 |
| 10,506,995 B2 * | 12/2019 | Ninomiya | .............. | A61B 6/547 |
| 2010/0329427 A1 | 12/2010 | Takae et al. | | |
| 2014/0098942 A1 | 4/2014 | Omura et al. | | |

FOREIGN PATENT DOCUMENTS

| | | |
|---|---|---|
| DE | 102010008552 A1 | 8/2011 |
| JP | 52-83673 U | 6/1977 |
| JP | 60-2505 U | 1/1985 |
| JP | 2004-73354 A | 3/2004 |
| JP | 2011-193996 A | 10/2011 |
| JP | 2012-29889 A | 2/2012 |
| JP | 2014-73322 A | 4/2014 |

OTHER PUBLICATIONS

International Search Report for PCT/JP2016/003454 dated Dec. 6, 2016 [PCT/ISA/210].
International Preliminary Report on Patentability dated Jan. 30, 2018 in counterpart international application No. PCT/JP2016/003454.
Written Opinion dated Dec. 6, 2016 issued by the International Searching Authority in corresponding application No. PCT/JP2016/003454.
Communication dated Aug. 10, 2018 from the European Patent Office in counterpart application No. 16830054.9.
Communication dated May 7, 2020, from the State Intellectual Property Office of the P.R.C in application No. 201680043798.5.

* cited by examiner

RADIATION-IRRADIATION DEVICE COMPRISING A FIRST ARM, A SECOND ARM, AND MAIN BODY SURFACE REGULATING A ROTATIONAL MOVEMENT OF THE SECOND ARM

CROSS REFERENCE TO RELATED APPLICATIONS

The present application is a Continuation of PCT International Application No. PCT/JP2016/003454 filed on Jul. 26, 2016, which claims priority under 35 U.S.C. § 119(a) to Japanese Patent Application No. 2015-147524 filed on Jul. 27, 2015. Each of the above applications is hereby expressly incorporated by reference, in its entirety, into the present application.

BACKGROUND

Technical Field

The present invention relates to a radiation-irradiation device that irradiates a subject with radiation in a case in which the radiation image of the subject is to be acquired.

Background Art

In the past, a portable radiation-irradiation device, on which only a minimum number of components for radiation irradiation, such as a radiation source and an electrical circuit, are mounted and which can be operated while being held with hands by an operator, has been proposed as disclosed in, for example, JP2012-029889A and "Toshiba Medical Supply Co., Ltd., X-ray equipment IPF-21, [on-line], [Search on Apr. 3, 2015], Internet <URL: http://www.toshiba-medical.co.jp/tmd/products/xray/mobile/ipf21/index.html>". Since this kind of portable radiation-irradiation device is reduced in weight so that an operator can hold and operate the radiation-irradiation device with hands, the radiation-irradiation device is advantageous for the imaging of a subject in various directions.

A radiation detector (so-called "Flat Panel Detector"), which records a radiation image representing a subject by being irradiated with radiation transmitted through the subject, is generally used in a case in which the radiation image of the subject is to be taken by this kind of radiation irradiation device. A cassette-type radiation detector having a structure in which an image detection unit and a control unit, such as a battery for drive and an electrical circuit relating to drive, are received in a housing is well known as the radiation detector. Further, in a case in which such a radiation detector is disposed at a position facing the radiation-irradiation device with a subject interposed therebetween and the radiation-irradiation device is driven in this state, the radiation detector is irradiated with radiation transmitted through the subject. Accordingly, a radiation image represented by the radiation transmitted through the subject is acquired.

The portable radiation-irradiation device can be held and operated with hands by an operator. However, a radiation-irradiation device, which includes a support device supporting a radiation source unit including a radiation source, is proposed to prevent shaking and to prevent the operator's hands or the like from being exposed to radiation. "Toshiba Medical Supply Co., Ltd., X-ray equipment IPF-21, [on-line], [Search on Apr. 3, 2015], Internet <URL:http://www-.toshiba-medical.co.jp/tmd/products/xray/mobile/ipf21/index.html>" also discloses an example of such a support device, and particularly, a support device that includes wheel parts provided at lower portions of support legs and can travel.

The radiation-irradiation device including the support device basically includes: a leg unit that is adapted to be capable of traveling using wheels; a body unit that receives a control unit including a battery for the drive of a radiation source, an electrical circuit relating to the drive of the radiation source, and the like and is held on the leg unit; and an arm unit that is connected to the body unit. The radiation source unit is mounted on the distal end of the arm unit.

A radiation-irradiation device, which has a structure in which an arm unit can be raised and lowered relative to a body of the device and can be folded to receive the radiation source unit so as to be compact in a case in which the radiation-irradiation device is not in use, is proposed. For example, in a device disclosed in JP2014-73322A, an arm unit is mounted on a device body by a raising/lowering mechanism including a rotational moving portion. Further, in devices disclosed in JP2011-193996A and JP2004-73354A, an arm unit is composed of a first arm and a second arm, which are rotatably mounted, a radiation source unit is mounted on the first arm, and the second arm is mounted on a device body by a raising/lowering mechanism including a rotational moving portion. Furthermore, in a device disclosed in JP2011-193996A, a raising/lowering mechanism is moved to the lowest position and a second arm is rotationally moved upward along a body in a case in which the device is not in use. Moreover, in a case in which the second arm is raised by the raising/lowering mechanism during the use of the device, the second arm is rotationally moved to allow the radiation source unit to be away from the body and moves the radiation source unit to a use position while maintaining the height of the radiation source unit. Further, the height of the radiation source unit can also be manually adjusted. Furthermore, in the device disclosed in JP2004-73354A, the radiation source unit can be moved to a desired position through the rotational movement of the first arm relative to the second arm and the rotational movement of the second arm relative to the raising/lowering mechanism even though the second arm is positioned at any height.

In a case in which the radiation-irradiation device is in use, first, the radiation-irradiation device is moved close to a bed for a patient. In this case, the arm unit is moved to the lowest position and is folded so as to not collide with various devices that are present in a hospital room. Then, in a case in which the radiation-irradiation device is in use, the arm unit is raised and the arm unit is rotationally moved to extend so that the radiation source unit is moved to a desired position above a subject. The radiation detector is moved to a desired position behind the subject so as to correspond to the radiation source unit. The radiation source is driven in this state and irradiates the subject with radiation, radiation transmitted through the subject is detected by the radiation detector, and the radiation image of the subject is acquired.

SUMMARY OF THE INVENTION

However, since the arm unit is merely rotationally moved relative to the raising/lowering mechanism in the device disclosed in JP2014-73322A, the moving range of the radiation source unit is narrow. For this reason, there is a case where it is difficult to move the radiation source unit to a desired position. Further, the raising/lowering and rotational movement of the second arm interlock with each other in the device disclosed in JP2011-193996A. Accordingly, in a case in which the bed on which the subject lies, various devices for treatment, or the like (hereinafter, referred to as a bed or the like) are present in a direction where the radiation source unit is moved, there is a possibility that the radiation source unit may collide with the bed or the like during the raising/lowering of the second arm. Furthermore, in a case in which the radiation source unit is to be lifted in the device disclosed in JP2004-73354A, there is a possibility that the radiation source unit may collide with the bed or the like in a case in which an operator does not give one's attention to the height of the second arm.

In this case, a method of moving the location of the device so that the radiation source unit does not collide with the bed or the like is considered. However, since a space near a bed is narrow in some imaging locations, such as an emergency room in which an urgent patient is to be imaged, there is a case where the device moved to a position near the bed cannot be easily moved.

The invention has been made in consideration of the above-mentioned circumstances, and an object of the invention is to prevent a radiation source unit from colliding with a bed or the like to allow the radiation source unit to be easily moved to a desired position in a radiation-irradiation device.

A radiation-irradiation device according to an aspect of the invention comprises a leg unit that is capable of traveling on a device-placement surface, a radiation source unit that irradiates a subject with radiation, an arm unit that supports the radiation source unit, an arm support unit that stands on the leg unit and supports the arm unit, and a raising/lowering mechanism that raises and lowers the arm unit relative to the arm support unit. The arm unit includes a first arm that is connected to the radiation source unit, a second arm, a first rotational moving portion that connects the first arm to the second arm so as to allow the first and second arms to be rotationally movable relative to each other, and a second rotational moving portion that connects the second arm to the raising/lowering mechanism so as to allow the second arm to be rotationally movable relative to the raising/lowering mechanism. The radiation-irradiation device further comprises regulating means for regulating the rotational movement of the second arm from an initial rotational movement position, which is performed using the second rotational moving portion, in a case in which the arm unit is positioned at a position other than a first position where the arm unit is raised or lowered by the raising/lowering mechanism.

In the invention, the arm unit includes the first arm that is connected to the radiation source unit, the second arm, the first rotational moving portion that connects the first arm to the second arm so as to allow the first and second arms to be rotationally movable relative to each other, and the second rotational moving portion that connects the second arm to the raising/lowering mechanism so as to allow the second arm to be rotationally movable relative to the raising/lowering mechanism. For this reason, the arm unit can be folded or be made to extend through the rotational movement of the first arm relative to the second arm and the rotational movement of the second arm relative to the raising/lowering mechanism.

The "initial rotational movement position" means the rotational movement position of the arm unit in a state in which the first and second arms are folded, preferably, a state in which the first and second arms are folded to the limit where the first and second arms are not rotationally moved any more. The rotational movement position of the arm unit in a state in which the second arm is rotationally moved upward so that the first and second arms are folded, preferably, a state in which the second arm is rotationally moved upward so that the first and second arms are folded to the limit where the first and second arms are not rotationally moved any more may be used as the initial rotational movement position. Further, the rotational movement position of the arm unit in a state in which the second arm is rotationally moved downward so that the first and second arms are folded, preferably, a state in which the second arm is rotationally moved downward so that the first and second arms are folded to the limit where the first and second arms are not rotationally moved any more may be used as the initial rotational movement position. Here, the fact that the second arm is rotationally moved upward means that the second arm is rotationally moved so that the first rotational moving portion is positioned above the second rotational moving portion. Furthermore, the fact that the second arm is rotationally moved downward means that the second arm is rotationally moved so that the first rotational moving portion is positioned below the second rotational moving portion.

"Regulating the rotational movement of the second arm" means that the rotational movement of the second arm to be performed using the second rotational moving portion cannot be performed. A direction where rotational movement is regulated may be only one direction about the rotational movement axis and may be both directions about the rotational movement axis. Here, if the rotational moving direction of the second arm in a case in which the second arm is rotationally moved upward from a state in which the second arm is rotationally moved downward is referred to as a first rotational moving direction, it is preferable that the rotational movement of the second arm in the first rotational moving direction is regulated in the invention. In a case in which the position of the second arm in a state in which the second arm is rotationally moved upward so that the first and second arms are folded is referred to as an initial rotational movement position, the first rotational moving direction is a direction where the second arm is rotationally moved toward the arm support unit. Further, the rotational movement of the second arm in a second rotational moving direction, which is a rotational moving direction opposite to the first rotational moving direction, in addition to the first rotational moving direction may be regulated.

In the radiation-irradiation device according to an aspect of the invention, the initial rotational movement position may be a position where the second arm is rotationally moved upward, and the regulating means may regulate the rotational movement of the second arm toward the arm support unit that is performed using the second rotational moving portion.

In this case, the regulating means may release the regulation of the rotational movement of the second arm toward the arm support unit that is performed using the second rotational moving portion in a case in which the arm unit is positioned at the first position.

Further, in the radiation-irradiation device according to an aspect of the invention, the regulating means may be formed of a surface of the arm support unit on which the arm unit is supported.

Furthermore, in the radiation-irradiation device according to an aspect of the invention, the first position may be the highest position in a raising/lowering range in which the arm unit is raised and lowered by the raising/lowering mechanism.

Moreover, in the radiation-irradiation device according to an aspect of the invention, the arm support unit may be a body unit that includes control means for controlling the radiation source unit.

The "control means" is means for performing control relating to the generation and irradiation of radiation, such as tube current, irradiation time, and a tube voltage, and is composed of, for example, a computer in which a program for control is installed, dedicated hardware, or a combination of both the computer and the dedicated hardware.

Further, in the radiation-irradiation device according to an aspect of the invention, the arm unit may be revolvably supported by the arm support unit.

Here, the arm support unit stands on the leg unit. In a case in which an axis extending in a direction where the arm support unit stands is prescribed, "revolution" means rotation about the axis.

The radiation-irradiation device may further comprise revolution regulating means for regulating revolution of the arm unit in a case in which the arm unit is positioned at a position other than the first position.

The radiation-irradiation device according to an aspect of the invention may further comprise first-rotational-moving-portion regulating means for regulating rotational movement of the first rotational moving portion.

The radiation-irradiation device according to an aspect of the invention may further comprise display means for displaying a movable range of the arm unit and the radiation source unit in a state in which the arm unit is viewed from a side.

Further, in the radiation-irradiation device according to an aspect of the invention, the display means may display a target position of the radiation source unit in a state in which the arm unit is viewed from a side.

The "side" means a direction parallel to the rotational movement axis of the first rotational moving portion or the second rotational moving portion.

The "target position" means a position at which an imaging unit is to be disposed in a case in which a subject is to be imaged. Specifically, the "target position" is a position at which the subject can be appropriately imaged, and can be determined depending on imaging conditions that are set on the basis of, for example, imaging request information and the like.

According to an aspect of the invention, the rotational movement of the second arm from an initial rotational movement position, which is performed using the second rotational moving portion, is regulated in a case in which the arm unit is positioned at a position other than a first position where the arm unit is raised or lowered by the raising/lowering mechanism. For this reason, it is possible to prevent the collision of the arm unit and the radiation source unit with the subject, the bed, and the like that is caused by the movement of the arm unit and the radiation source unit. Further, since the rotational movement of the second arm is not regulated in a case in which the arm unit is positioned at the first position where the arm unit is raised or lowered, the arm unit and the radiation source unit can be moved while avoiding the subject, the bed, and the like. Accordingly, according to an aspect of the invention, the radiation source unit can be easily moved to a desired position.

DESCRIPTION OF EMBODIMENTS

Figure 1:
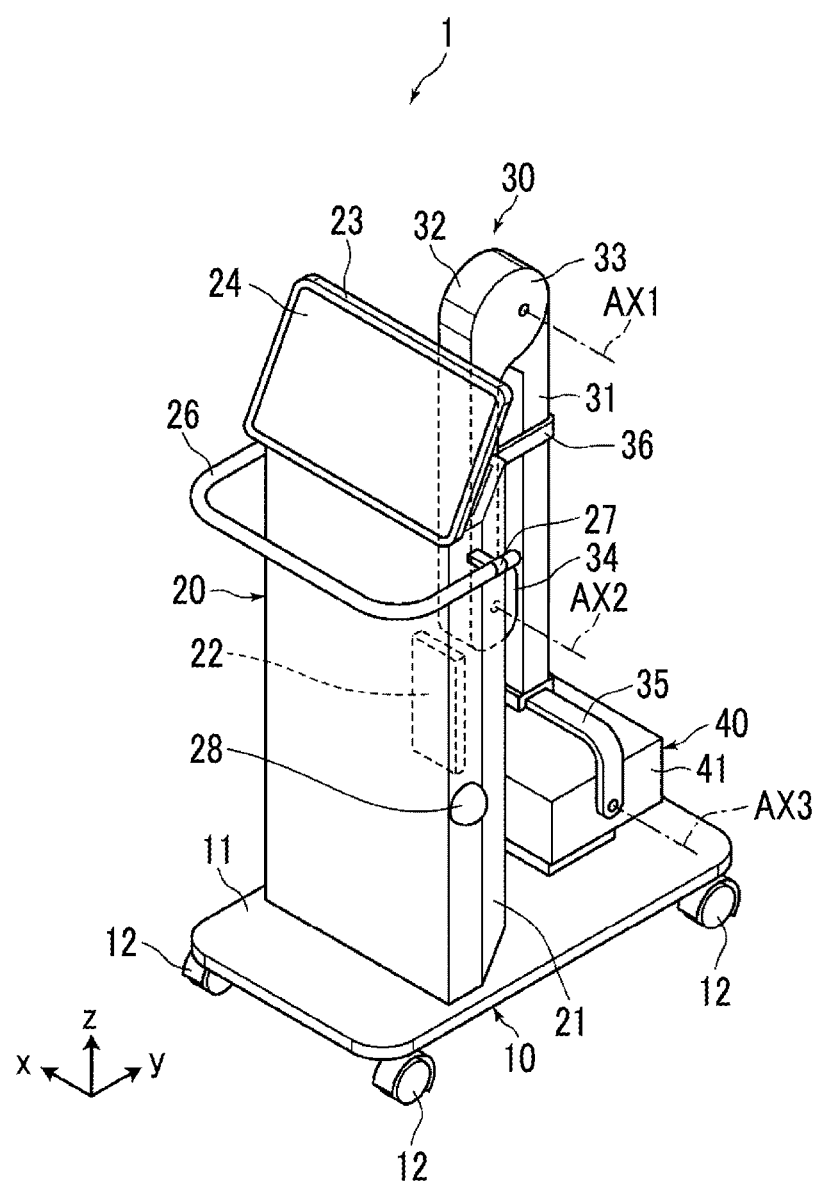
FIG. 1 is a perspective view showing a shape of an entire radiation-irradiation device according to an embodiment of the invention.
Figure 2:
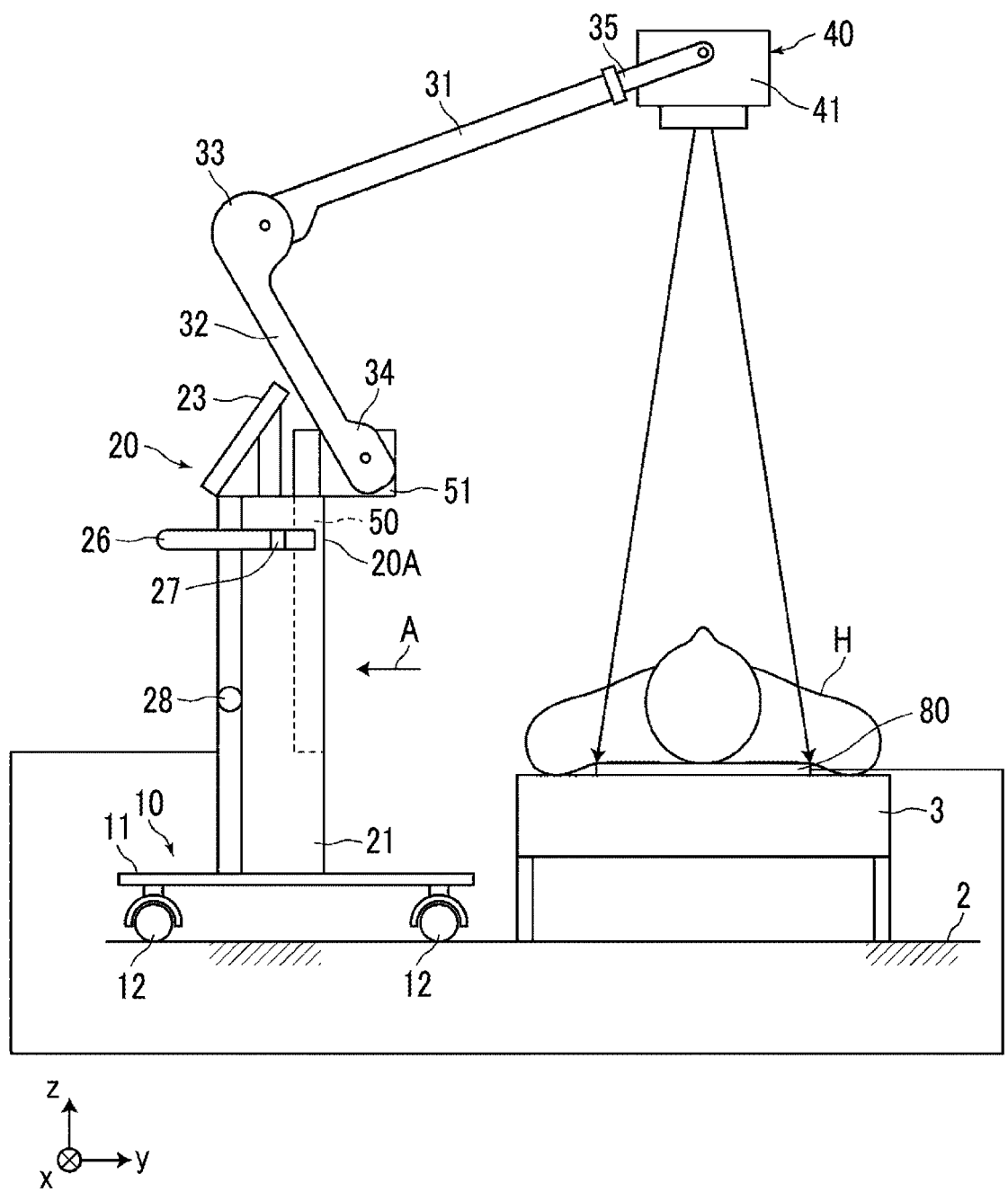
FIG. 2 is a diagram showing a state in which the radiation-irradiation device according to the embodiment of the invention is in use.

An embodiment of the invention will be described below with reference to the drawings. FIG. 1 is a perspective view showing the shape of the entire radiation-irradiation device according to an embodiment of the invention that is not in use, and FIG. 2 is a side view showing a state in which the radiation-irradiation device according to the embodiment of the invention is in use. In the following description, the upper side and the lower side in a vertical direction in a state in which the radiation-irradiation device is placed on a device-placement surface, such as the floor of, for example, a medical facility are referred to as "upper" and "lower", and a direction perpendicular to the vertical direction in the same state as the state is referred to as a "horizontal" direction. Further, a coordinate system in which the vertical direction is a z direction, a lateral direction of FIG. 2 is a y direction, and a direction perpendicular to the plane of FIG. 2 is an x direction is set in the following description.

As shown in FIG. 1, a radiation-irradiation device 1 according to this embodiment includes a leg unit 10, a body unit 20, an arm unit 30, and a radiation source unit 40.

The leg unit 10 can travel on the device-placement surface 2, and includes a plate-like base 11 and four wheel parts 12 that are mounted on four corners of the lower surface of the plate like base 11. Each of the wheel parts 12 is formed of a rubber tire or the like, and is mounted on the plate like base 11 so as to be revolvable about an axis, which extends in the vertical direction, in a horizontal plane. Accordingly, the leg unit 10 is adapted to be capable of traveling on the device-placement surface 2 in an arbitrary direction.

The body unit 20 stands on the leg unit 10, and includes a housing 21. A control unit 22, which controls the drive of the radiation-irradiation device 1, and a battery (hereinafter, simply referred to as a control unit 22) are received in the housing 21.

The control unit 22 is a unit that performs control relating to the generation and irradiation of radiation, such as tube current, irradiation time, and a tube voltage of the radiation source unit 40, and control relating to the acquisition of a radiation image, such as image processing for a radiation image acquired by a radiation detector 80. The control unit 22 is composed of, for example, a computer in which a program for control is installed, dedicated hardware, or a combination of both the computer and the dedicated hardware.

Further, a monitor 23 is mounted on the upper surface of the housing 21. Furthermore, a handle 26, which is used to push or pull the radiation-irradiation device 1, is mounted on the upper portion of the housing 21 by an adapter 27. Moreover, omnidirectional cameras 28, which are used to take omnidirectional images of the radiation-irradiation device 1, are mounted on both side surfaces of the body unit 20. Only one omnidirectional camera 28 is shown in FIGS. 1 and 2.

The monitor 23 is formed of a liquid crystal panel or the like, and displays a radiation image that is acquired from the imaging of a subject H and various kinds of information that is required for the control of the radiation-irradiation device 1. Further, the monitor 23 includes a touch panel type input part 24, and receives the input of various commands required for the operation of the radiation-irradiation device 1. Specifically, the monitor 23 receives an input for the setting of imaging conditions and an input for imaging, that is, the emission of radiation. The monitor 23 corresponds to display means. The monitor 23 is mounted on the upper surface of the body unit 20 so that the inclination and the rotational position of the monitor 23 are changeable. Further, the monitor 23 may include buttons, which are used to perform various operations, and the like as the input part 24 instead of the touch panel type input part 24.

The arm unit 30 is supported on the body unit 20. In detail, the arm unit 30 is supported on the surface of the body unit 20 opposite to the handle 26, that is, a right surface 20A of the body unit 20 in FIG. 2. For this reason, the body unit 20 composes an arm support unit according to the invention in this embodiment. The arm unit 30 is adapted to be capable of being raised and lowered relative to the body unit 20 by a raising/lowering mechanism 50. The arm unit 30 includes a first arm 31, a second arm 32, a first rotational moving portion 33, a second rotational moving portion 34, and a mounting part 35. The radiation source unit 40 is connected to the distal end of the first arm 31 by the mounting part 35. In the following description, an end portion of the first arm 31 close to the radiation source unit 40 is referred to as an upper end portion and an end portion of the first arm 31 close to the second arm 32 is referred to as a lower end portion. Further, an end portion of the second arm 32 close to the first arm 31 is referred to as an upper end portion and an end portion of the second arm 32 close to the body unit 20 is referred to as a lower end portion.

The first arm 31 and the second arm 32 are connected to each other by the first rotational moving portion 33 so as to be rotationally movable about a rotational movement axis AX1. The rotational movement axis AX1 is an axis extending in the x direction. The first arm 31 is rotationally moved about the rotational movement axis AX1 so that an angle between the first arm 31 and the second arm 32 is changed. The first rotational moving portion 33 holds both the first arm 31 and the second arm 32 so that the first arm 31 is rotationally moved relative to the second arm 32 through a friction mechanism. For this reason, the first arm 31 is rotationally movable in a case in which an external force, which is strong to some extent, is applied to the first arm 31, and maintains an angle relative to the second arm 32 without being rotationally moved as long as an external force is not applied to the first arm 31.

The second arm 32 is connected to an adapter 51, which is mounted on the upper end portion of the raising/lowering mechanism 50, through the second rotational moving portion 34 so as to be rotationally movable about a rotational movement axis AX2. The rotational movement axis AX2 is an axis extending in the x direction. The second arm 32 is rotationally moved about the rotational movement axis AX2 so that an angle between the second arm 32 and the right surface 20A of the body unit 20 on which the arm unit 30 is supported is changed. The second rotational moving portion 34 holds both the second arm 32 and the body unit 20 so that the second arm 32 is rotationally moved relative to the body unit 20 through a friction mechanism. For this reason, the second rotational moving portion 34 is rotationally movable in a case in which an external force, which is strong to some extent, is applied to the second rotational moving portion 34, and maintains an angle relative to the body unit 20 without being rotationally moved as long as an external force is not applied to the second rotational moving portion 34.

Figure 3:
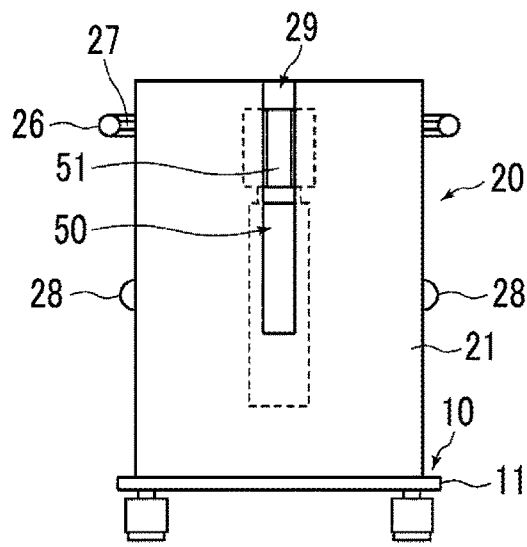
FIG. 3 is a diagram viewed in a direction of arrow A of FIG. 2.

FIG. 3 is a diagram viewed in the direction of arrow A of FIG. 2. As shown in FIG. 3, a groove 29, through which the adapter 51 can pass at the time of an operation for raising and lowering the arm unit 30 performed by the raising/lowering mechanism 50, is formed on the right surface 20A of the body unit 20 in FIG. 2. For illustration, the monitor 23 and the arm unit 30 are not shown in FIG. 3.

The mounting part 35 is formed in a U shape, and is mounted on the distal end of the first arm 31. The radiation source unit 40 is connected to the distal end of the first arm 31 through the mounting part 35 so as to be rotationally movable about a rotational movement axis AX3. The rotational movement axis AX3 is an axis extending in the x direction. The radiation source unit 40 is rotationally moved about the rotational movement axis AX3 so that an angle between the radiation source unit 40 and the first arm 31 is changed. The mounting part 35 holds both the radiation source unit 40 and the first arm 31 so that the radiation source unit 40 is rotationally moved relative to the first arm 31 through a friction mechanism. For this reason, the radiation source unit 40 is rotationally movable in a case in which an external force, which is strong to some extent, is applied to the radiation source unit 40, and maintains an angle relative to the first arm 31 without being rotationally moved as long as an external force is not applied to the radiation source unit 40.

The rotational movement between the first arm 31 and second arm 32 and the rotational movement between the first arm 31 and the radiation source unit 40 are achieved through the friction mechanisms, but the rotational movement positions of the first arm 31, the second arm 32, and the radiation source unit 40 may be fixed by publicly known lock mechanisms. In this case, the rotational movement between the first and second arms 31 and 32 and the rotational movement between the first arm 31 and the radiation source unit 40 can be performed in a case in which the lock mechanisms are released. Further, the rotational movement positions can be fixed in a case in which the lock mechanisms are locked at desired rotational movement positions.

Here, the arm unit 30 is positioned at the lowest position of the raising/lowering mechanism 50 in a case in which the radiation-irradiation device 1 shown in FIG. 1 is not in use. Further, the rotational movement position of the arm unit 30 is an initial rotational movement position.

The initial rotational movement position is the rotational movement position of the arm unit 30 in a state in which the first arm 31 and second arm 32 are folded. Particularly, in this embodiment, the initial rotational movement position is set to the rotational movement position of the arm unit 30 in a state in which the first arm 31 and second arm 32 are folded to the limit where the first arm 31 and second arm 32 are not rotationally moved any more as shown in FIG. 1. At the initial rotational movement position, the second arm 32 is rotationally moved so that the first rotational moving portion 33 is positioned above the second rotational moving portion 34.

The first arm 31 and second arm 32 are connected to each other by a connecting belt 36 at the initial rotational movement position. For example, one end portion of the connecting belt 36 is mounted on the second arm 32 and a hook-and-loop fastener is mounted on the other end portion of the connecting belt 36. A hook-and-loop fastener corresponding to the hook-and-loop fastener of the connecting belt 36 is mounted on the opposite surface of the first arm 31 in FIG. 1. Further, the connecting belt 36 is put around the first arm 31 from the right surface of the first arm 31 in FIG. 1 to the opposite surface of the first arm 31 to connect the hook-and-loop fastener of the connecting belt 36 to the hook-and-loop fastener mounted on the first arm 31. Accordingly, the first arm 31 is not rotationally moved relative to the second arm 32 at the initial rotational movement position. The connecting belt 36 corresponds to first-rotational-moving-portion regulating means.

The radiation source unit 40 has a structure where a radiation source, a collimator for narrowing the irradiation range of radiation, and the like are received in a housing 41. The radiation source is composed of, for example, an X-ray tube, a booster circuit, cooling means for cooling the X-ray tube, and the like. The emission of radiation from the radiation source of the radiation source unit 40 is performed by a command that is sent from the input part 24 of the monitor 23 by an operator.

Figure 4:
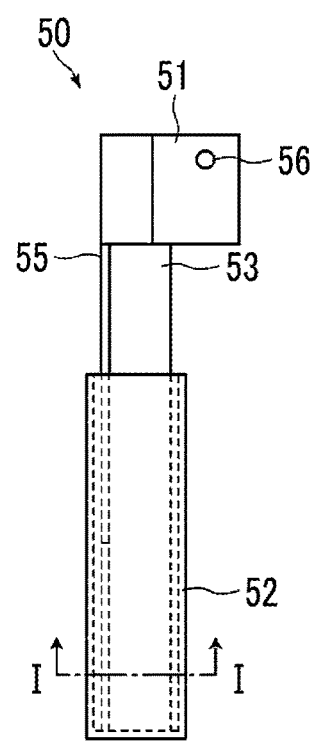
FIG. 4 is a side view showing a structure of a raising/lowering mechanism.
Figure 5:
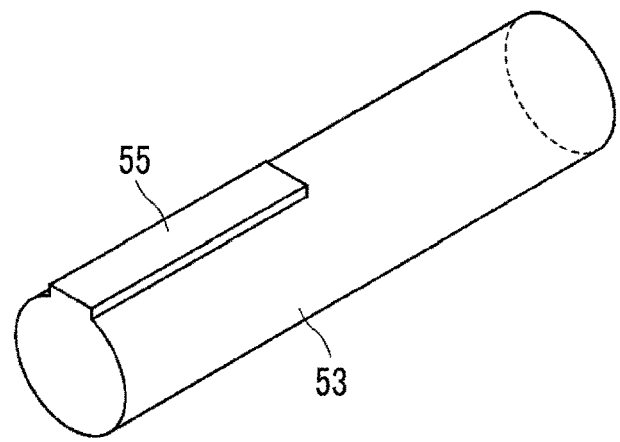
FIG. 5 is a perspective view showing the structure of a shaft.
Figure 6:
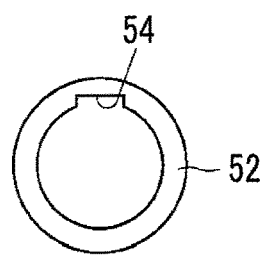
FIG. 6 is a cross-sectional view taken along line I-I of FIG. 4.

FIG. 4 is a side view showing the structure of the raising/lowering mechanism 50, FIG. 5 is a perspective view showing the structure of a shaft that composes the raising/lowering mechanism 50, and FIG. 6 is a cross-sectional view taken along line I-I of FIG. 4. As shown in FIG. 4, the raising/lowering mechanism 50 includes an outer cylinder 52 that is mounted inside the body unit 20, a shaft 53 that is fitted to the outer cylinder 52, and the adapter 51 that is mounted on the upper end portion of the shaft 53. A hole 56 is formed in the adapter 51 at a position corresponding to the rotational movement axis AX2 of the second rotational moving portion 34.

The shaft 53 is movable relative to the outer cylinder 52 in the vertical direction, and the position of the shaft 53 relative to the outer cylinder 52 in the vertical direction can be fixed at a desired position by a lock mechanism (not shown).

A key way 54 is formed in the outer cylinder 52, and a key 55 to be engaged with the key way 54 is formed on the shaft 53. The key 55 is formed so as to have a predetermined length from the upper end of the shaft 53. Here, the key 55 has a length that allows the lower end of the key 55 to be positioned above the upper end of the outer cylinder 52 in a state in which the shaft 53 reaches the highest position. For this reason, since the key 55 is engaged with the key way 54 until the shaft 53 reaches the highest position, the shaft 53 is not rotated relative to the outer cylinder 52 about the central axis thereof. However, since the key 55 deviates from the key way 54 in a case in which the shaft 53 reaches the highest position, the shaft 53 is rotatable relative to the outer cylinder 52 about the central axis thereof. Accordingly, the arm unit 30 mounted on the raising/lowering mechanism 50 is revolvable relative to the body unit 20. Revolution means rotation about the axis of the shaft 53, that is, a z axis that is an axis perpendicular to the device-placement surface 2. Further, the key way 54 of the outer cylinder 52 and the key 55 of the shaft 53 correspond to revolution regulating means.

In this embodiment, the radiation detector 80 is disposed under a subject H supine on a bed 3 and is irradiated with radiation (for example, X-rays) emitted from the radiation source unit 40 through the subject H as shown in FIG. 2, so that the subject is imaged. The radiation detector 80 and the radiation-irradiation device 1 are connected to each other in a wireless or wired manner. Accordingly, the radiation image of the subject H, which is acquired by the radiation detector 80, is directly input to the device 1.

Figure 7:
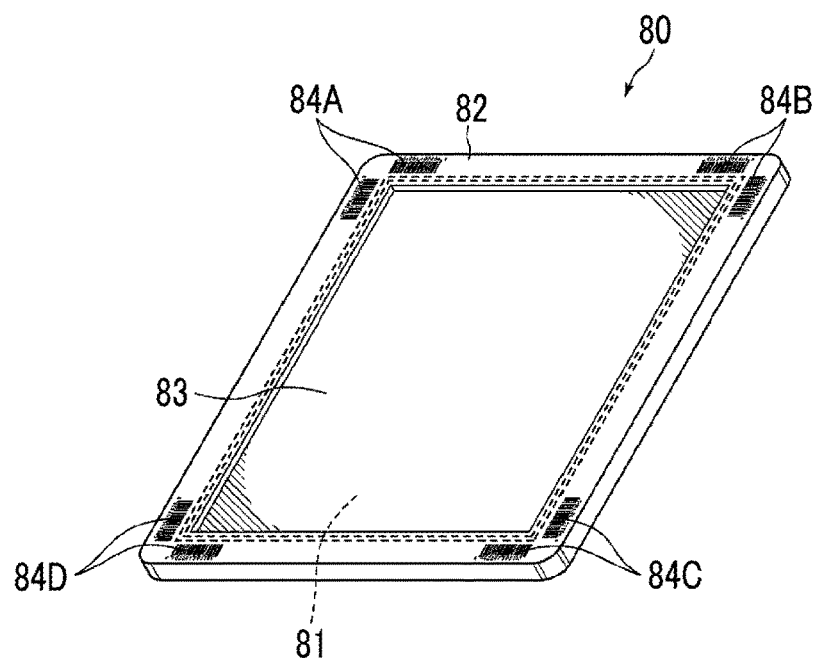
FIG. 7 is a perspective view showing an appearance of a radiation detector viewed from the front surface that is a radiation-irradiation side.

The radiation detector 80 will be briefly described here with reference to FIG. 7. FIG. 7 is a perspective view showing the appearance of the radiation detector viewed from the front surface that is a radiation-irradiation side. The radiation detector 80 is a cassette-type radiation detector that includes a housing 82 receiving an image detection unit 81 as shown in FIG. 7. As well known, the image detection unit 81 includes a scintillator (phosphor) that converts incident radiation into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate.

An imaging control unit and the like are built in the housing 82 in addition to the image detection unit 81. The imaging control unit includes a gate driver that applies gate pulses to a gate of a TFT to switch the TFT, a signal processing circuit that converts the electric charges accumulated in the pixels into analog electrical signals representing an X-ray image and outputs the analog electrical signals, and the like. Further, the housing 82 has substantially the same size as, for example, a film cassette, an imaging plate (IP) cassette, or a computed radiography (CR) cassette that is based on International Organization for Standardization (ISO) 4090:2001.

Markers 84A to 84D, which represent identification information for identifying the radiation detector 80, are given to four corners of a front surface 82A of the housing 82. In this embodiment, the markers 84A to 84D are formed of two bar codes orthogonal to each other, respectively.

Next, an operation in a case in which a radiation image is not yet taken by the radiation-irradiation device 1 of this embodiment will be described. In the state which is shown in FIG. 1 and in which the radiation-irradiation device 1 is not in use, the radiation-irradiation device 1 is carried to a use position while being made to travel on the device-placement surface 2, such as the floor of a hospital, by the wheel parts 12 of the leg unit 10. In this case, since the wheel parts 12 are revolvably mounted on the base 11 as described above, the radiation-irradiation device 1 can be moved in a front-back direction and the lateral direction and can also be moved along a large curve. Further, the radiation-irradiation device 1 can also revolve at that position. Accordingly, the radiation-irradiation device 1 can be quickly carried to a use position in a state in which the radiation-irradiation device 1 revolves in a small radius.

The taking of a radiation image is performed on the subject H who is supine on the bed 3 as shown in the above-mentioned FIG. 2. In a case in which the radiation-irradiation device 1 is to be set close to the subject H, the radiation-irradiation device 1 can also be moved in the height direction of a subject H by the wheel parts 12. Accordingly, the radiation-irradiation device 1 can be easily set to the optimum position.

Figure 8:
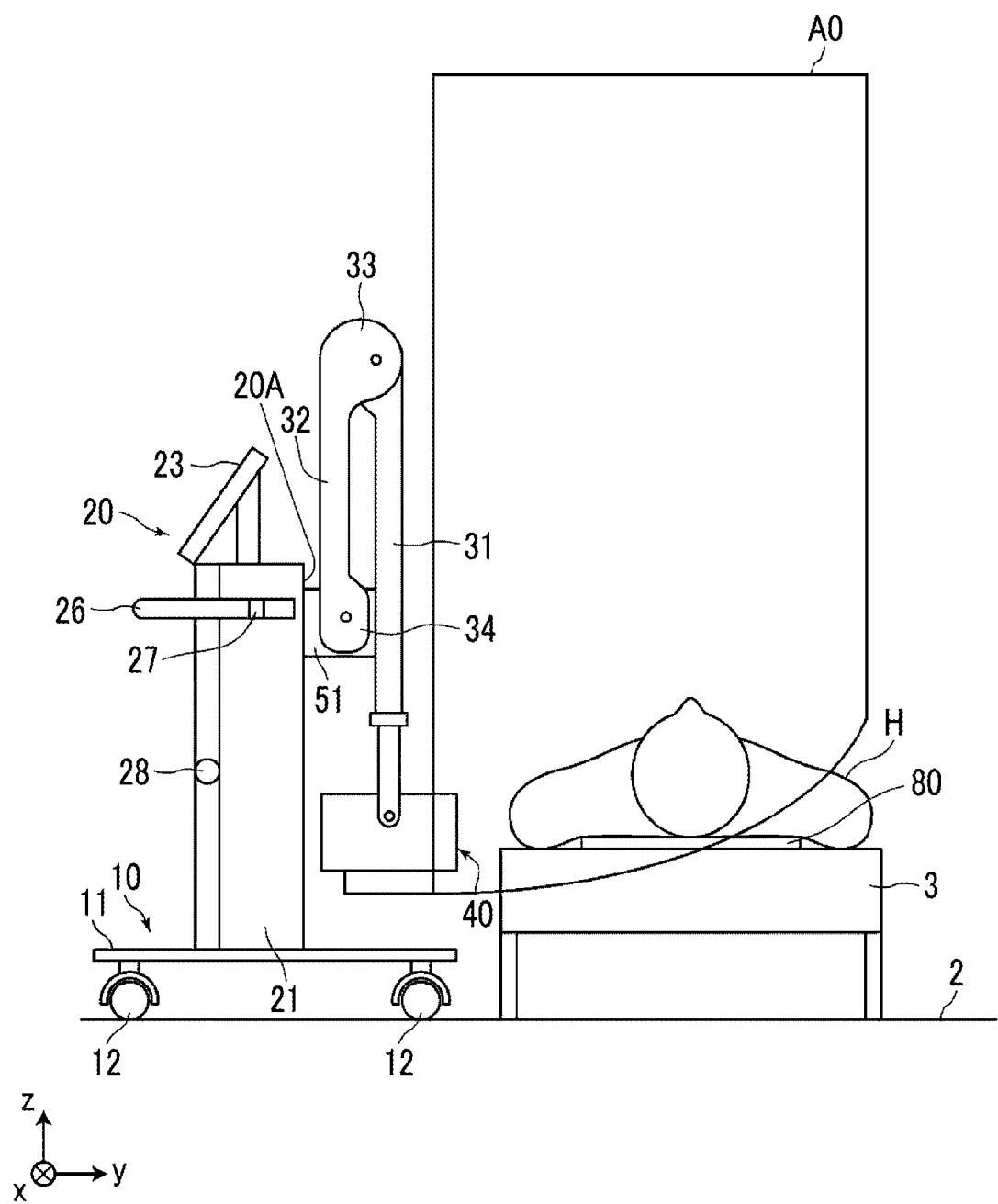
FIG. 8 is a schematic side view illustrating an operation for moving an arm unit and a radiation source unit of the radiation-irradiation device.

FIGS. 8 to 11 are schematic side views illustrating an operation for moving the arm unit 30 and the radiation source unit 40 of the radiation-irradiation device 1. FIGS. 8 to 11 are side views of the device 1 viewed in the x direction. The movable range A0 of both the arm unit 30 and the radiation source unit 40 viewed in the x direction is shown in FIGS. 8 to 11. First, the arm unit 30 is positioned at the lowest position of the raising/lowering mechanism 50 in a state shown in FIG. 8. Further, the rotational movement position of the arm unit is the above-mentioned initial rotational movement position. A state in which the arm unit 30 is positioned at the lowest position of the raising/lowering mechanism 50 and is positioned at the above-mentioned initial rotational movement position corresponds to the initial position of the arm unit 30. At the initial position of the arm unit 30, the movable range A0 of the radiation source unit 40 overlaps the subject H and the bed 3 as shown in FIG. 8. For this reason, the radiation source unit 40 collides with the subject H and the bed 3 in a case in which the second arm 32 is rotationally moved toward the body unit 20.

However, in this embodiment, the rotational movement of the second arm 32 from the initial rotational movement position performed using the second rotational moving portion 34 is regulated in a case in which the arm unit 30 is not positioned at the highest position in a raising/lowering range in which the arm unit 30 is raised and lowered by the raising/lowering mechanism 50. That is, the second arm 32 collides with the surface 20A of the body unit 20 on which the arm unit 30 is supported in a case in which the second arm 32 is rotationally moved about the rotational movement axis AX2 to the body unit 20. Accordingly, in a case in which the arm unit 30 is positioned at the lowest position, the second arm 32 cannot be rotationally moved from the initial rotational movement state of the arm unit 30. For this reason, the radiation source unit 40 cannot be moved up through the rotational movement of the second arm 32 about the rotational movement axis AX2. The surface 20A of the body unit 20 on which the arm unit 30 is supported composes regulating means of the invention.

Figure 9:
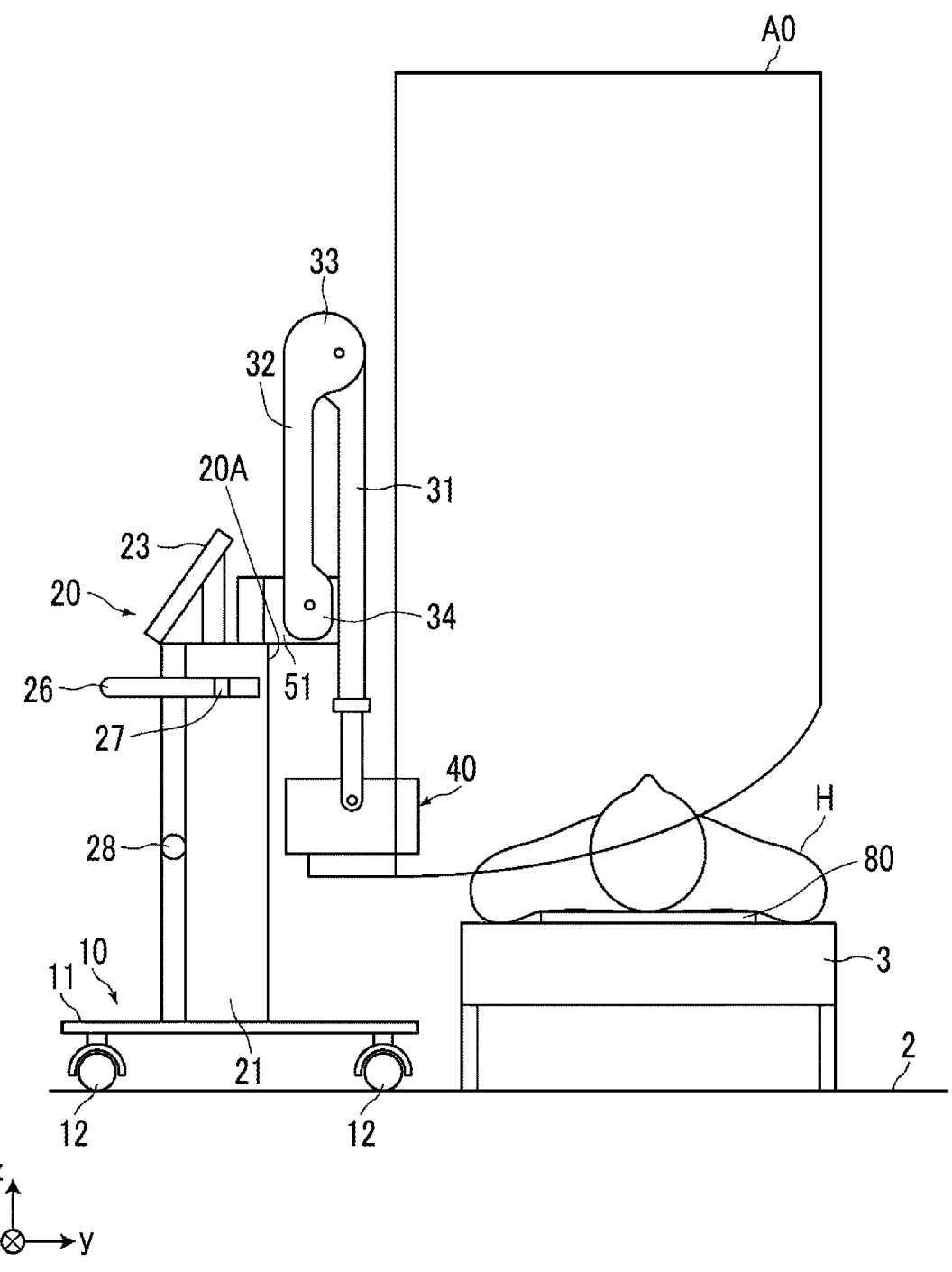
FIG. 9 is a schematic side view illustrating the operation for moving the arm unit and the radiation source unit of the radiation-irradiation device.
Figure 10:
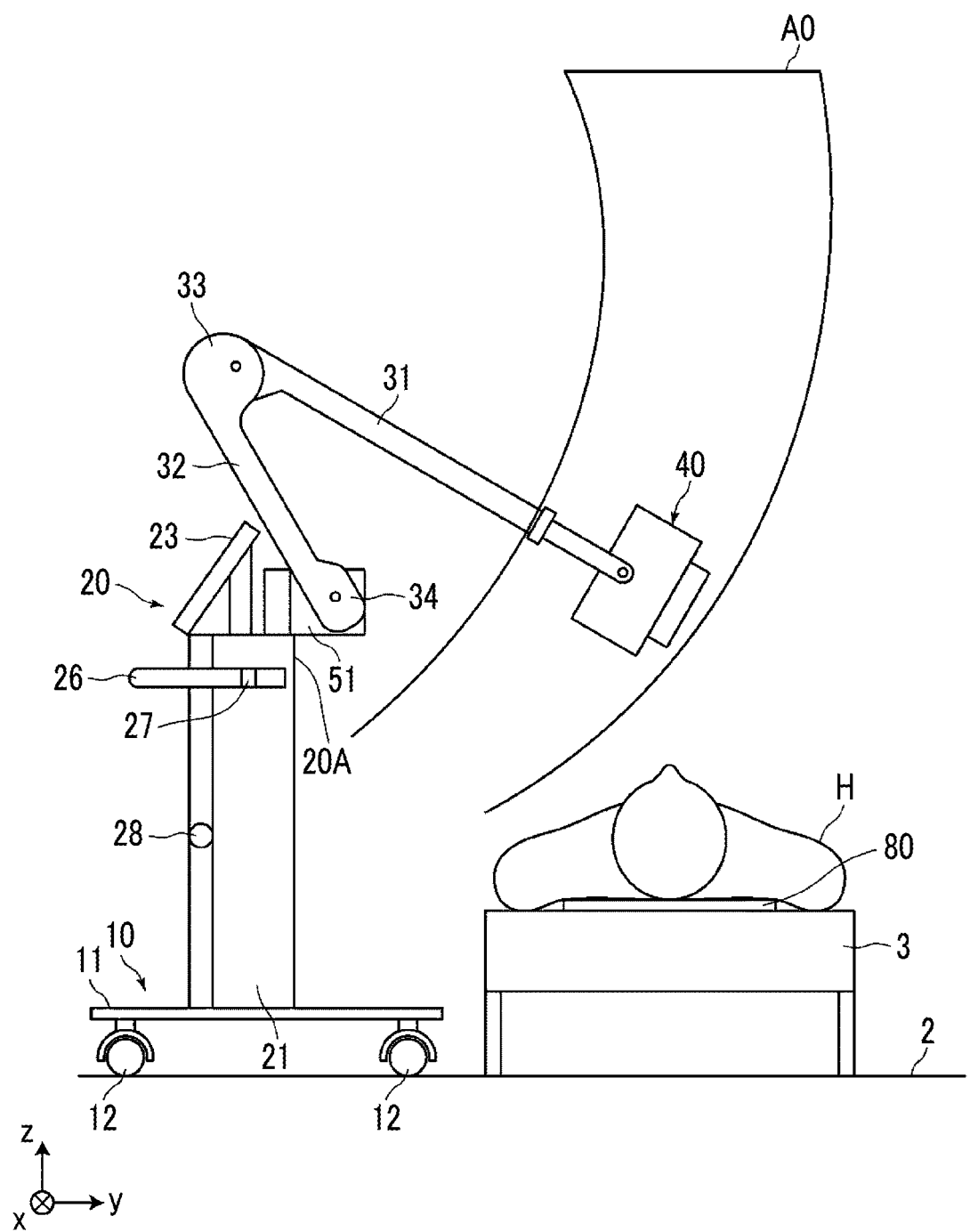
FIG. 10 is a schematic side view illustrating the operation for moving the arm unit and the radiation source unit of the radiation-irradiation device.
Figure 11:
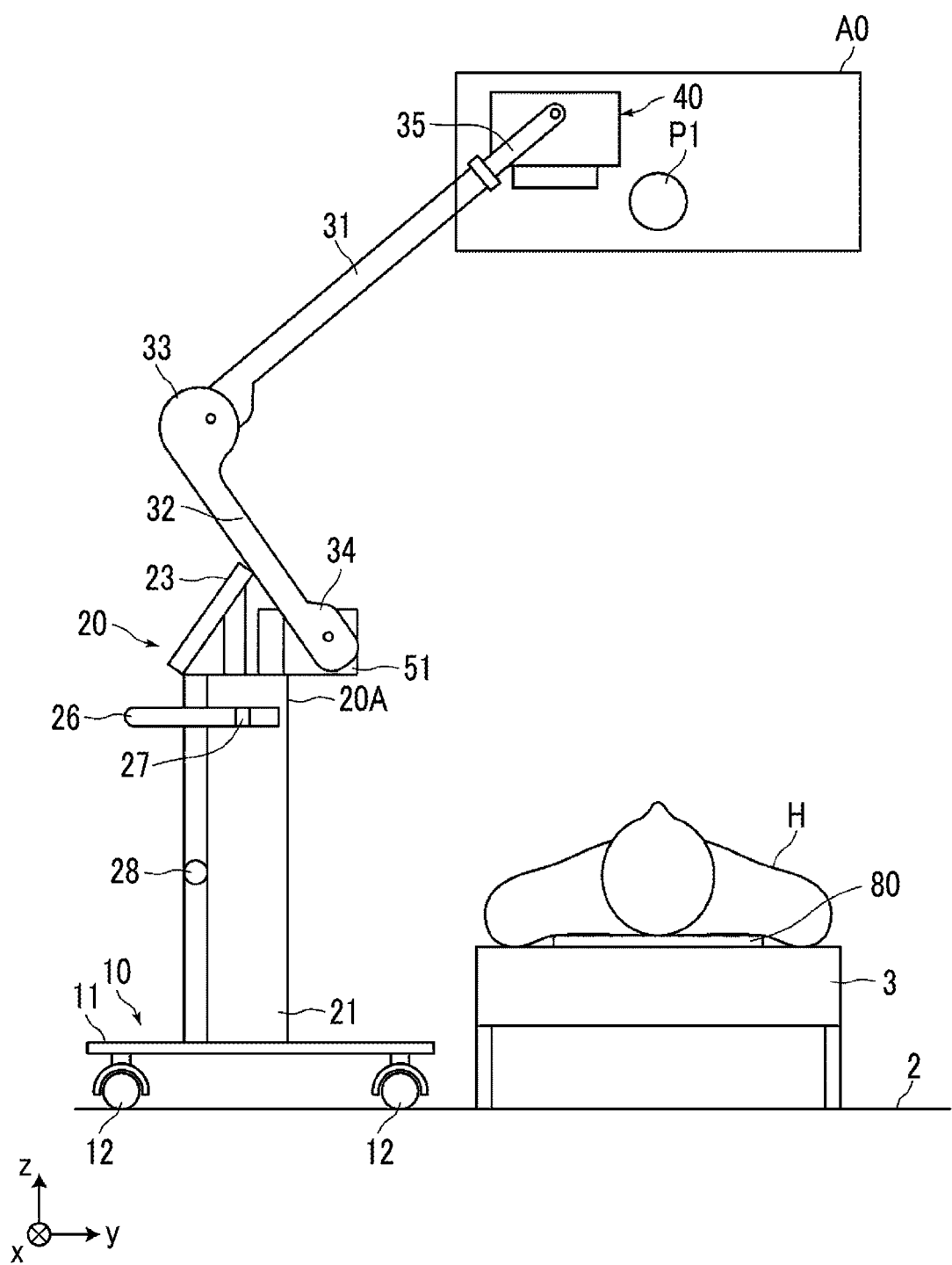
FIG. 11 is a schematic side view illustrating the operation for moving the arm unit and the radiation source unit of the radiation-irradiation device.

An operator raises the arm unit 30 relative to the body unit 20 from the initial position of the arm unit 30 shown in FIG. 8 by the raising/lowering mechanism 50. FIG. 9 is a side view showing a state in which the arm unit 30 is raised to the highest position serving as a first position. In this state, the movable range A0 of the radiation source unit 40 overlaps the subject H. Here, in a case in which the arm unit 30 is positioned at the highest position as shown in FIG. 9 and the second arm 32 is rotated about the rotational movement axis AX2 in a counterclockwise direction in FIG. 9 from the initial rotational movement state, the second arm 32 does not collide with the surface 20A of the body unit 20 on which the arm unit 30 is supported. For this reason, the second arm 32 can be rotationally moved over the body unit 20 about the rotational movement axis AX2 as shown in FIG. 10. Accordingly, the radiation source unit 40 is moved toward the upper left side of the subject H that is away from the subject H. In addition, the operator can further move the radiation source unit 40 up without making the radiation source unit 40 collide with the subject H and the bed 3 as shown in FIG. 11 by rotationally moving the first arm 31 about the rotational movement axis AX1 after removing the connecting belt 36.

The operator rotationally moves the first arm 31 about the rotational movement axis AX1 and rotationally moves the second arm 32 about the rotational movement axis AX2 by pulling the radiation source unit 40 in the y direction in this state, so that the operator can move the radiation source unit 40 to a target position P1 directly above the subject H.

Further, after the radiation source unit 40 is moved to the target position P1, the radiation source unit 40 is driven by a command sent from the input part 24 and irradiates the subject H with radiation. Then, the radiation transmitted through the subject H is detected by the radiation detector 80, so that the radiation image of the subject H can be acquired.

As described above, in this embodiment, the rotational movement of the second arm 32 from the initial rotational movement position performed using the second rotational moving portion 34 is regulated in a case in which the arm unit 30 is positioned at a position other than the first position where the arm unit 30 is raised by the raising/lowering mechanism 50, that is, the highest position. For this reason, since the second arm 32 is not rotationally moved in a case in which the arm unit 30 is positioned at a position other than the highest position, the arm unit 30 and the radiation source unit 40 are not moved. Accordingly, it is possible to prevent the collision of the arm unit 30 and the radiation source unit 40 with the subject H and the bed 3, which is caused by the movement of the arm unit 30 and the radiation source unit 40, in a case in which the arm unit 30 is positioned at a position other than the highest position. Further, the second arm 32 can be rotationally moved toward the body unit 20 in a case in which the arm unit 30 is positioned at the highest position. For this reason, in a case in which only the second arm 32 is rotationally moved toward the body unit 20, the radiation source unit 40 in addition to the entire arm unit 30 are moved in a direction where the radiation source unit 40 is away from the subject H. After that, the first arm 31 is rotationally moved using the first rotational moving portion 33, so that the radiation source unit 40 can be moved in a direction where the radiation source unit 40 is lifted without colliding with the subject H, the bed 3, and the like. Accordingly, according to this embodiment, the radiation source unit 40 can be easily moved to a desired position.

Further, since the rotational movement of the second arm 32 is regulated by the surface 20A of the body unit 20 on which the arm unit 30 is supported, means for regulating the movement of the radiation source unit 40 does not need to be separately provided. Accordingly, the structure of the device 1 can be simplified.

Furthermore, since the movement of the first arm 31 and the radiation source unit 40 in a direction where the first arm 31 and the radiation source unit 40 are away from the second arm 32, which is caused by the rotational movement of the first arm 31 relative to the second arm 32, can be regulated by the connecting belt 36, it is possible to more reliably prevent the collision of the first arm 31 and the radiation source unit 40 with the bed 3 for the subject H and the like that is caused by the movement of the first arm 31 and the radiation source unit 40.

Only the rotational movement of the second arm 32 from the initial rotational movement position toward the body unit 20 is regulated in the embodiment, but a lock mechanism or the like may be provided to regulate the rotational movement of the second arm 32 toward the side opposite to the body unit 20, that is, the clockwise rotation of the second arm 32 about the rotational movement axis AX2 in FIG. 2 in addition to the rotational movement of the second arm 32 toward the body unit 20.

Further, the movable range A0 of the arm unit 30 and the radiation source unit 40 shown in FIGS. 8 to 11 may be displayed on the monitor 23 in this embodiment. For this purpose, the arm unit 30 is provided with a sensor for detecting the position of the second rotational moving portion 34 that is set by the raising/lowering mechanism 50, a sensor for detecting a first rotational movement angle that is the rotational movement angle of the first arm 31 relative to the first rotational moving portion 33, and a sensor for detecting a second rotational movement angle that is the rotational movement angle of the second arm 32 relative to the second rotational moving portion 34. Furthermore, the image of the radiation-irradiation device 1, which is viewed from the side, is generated in the control unit 22 by using images that are taken by the omnidirectional cameras 28. Here, the omnidirectional cameras 28 take the all-round images of the device 1, and input the images, which are acquired from imaging, to the control unit 22 of the body unit 20. Since two omnidirectional cameras 28 are mounted on the body unit 20 in this embodiment, two images are input to the control unit 22. The control unit 22 creates a side image A1 of the radiation-irradiation device 1, which is viewed from the side, from the two images input.

The sensors detect the position of the second rotational moving portion 34 that is set by the raising/lowering mechanism 50, the first rotational movement angle that is the rotational movement angle of the first arm 31 relative to the first rotational moving portion 33, and the second rotational movement angle that is the rotational movement angle of the second arm 32 relative to the second rotational moving portion 34, respectively. The first rotational movement angle and second rotational movement angle are angles that are based on a raised or lowered position and a rotational movement position at, for example, the above-mentioned initial position of the arm unit 30. The sensors input the detected position of the second rotational moving portion 34, the detected first rotational movement angle, and the detected second rotational movement angle to the control unit 22.

The lengths of the first arm 31 and the second arm 32 and the size of the radiation source unit 40 are stored in the control unit 22 in advance. Further, the control unit 22 calculates the movable range A0 of the arm unit 30 and the radiation source unit 40 from the position of the second rotational moving portion 34, the first rotational movement angle, and the second rotational movement angle, which are input from the sensors, and the lengths of the first and second arms 31 and 32.

Figure 12:
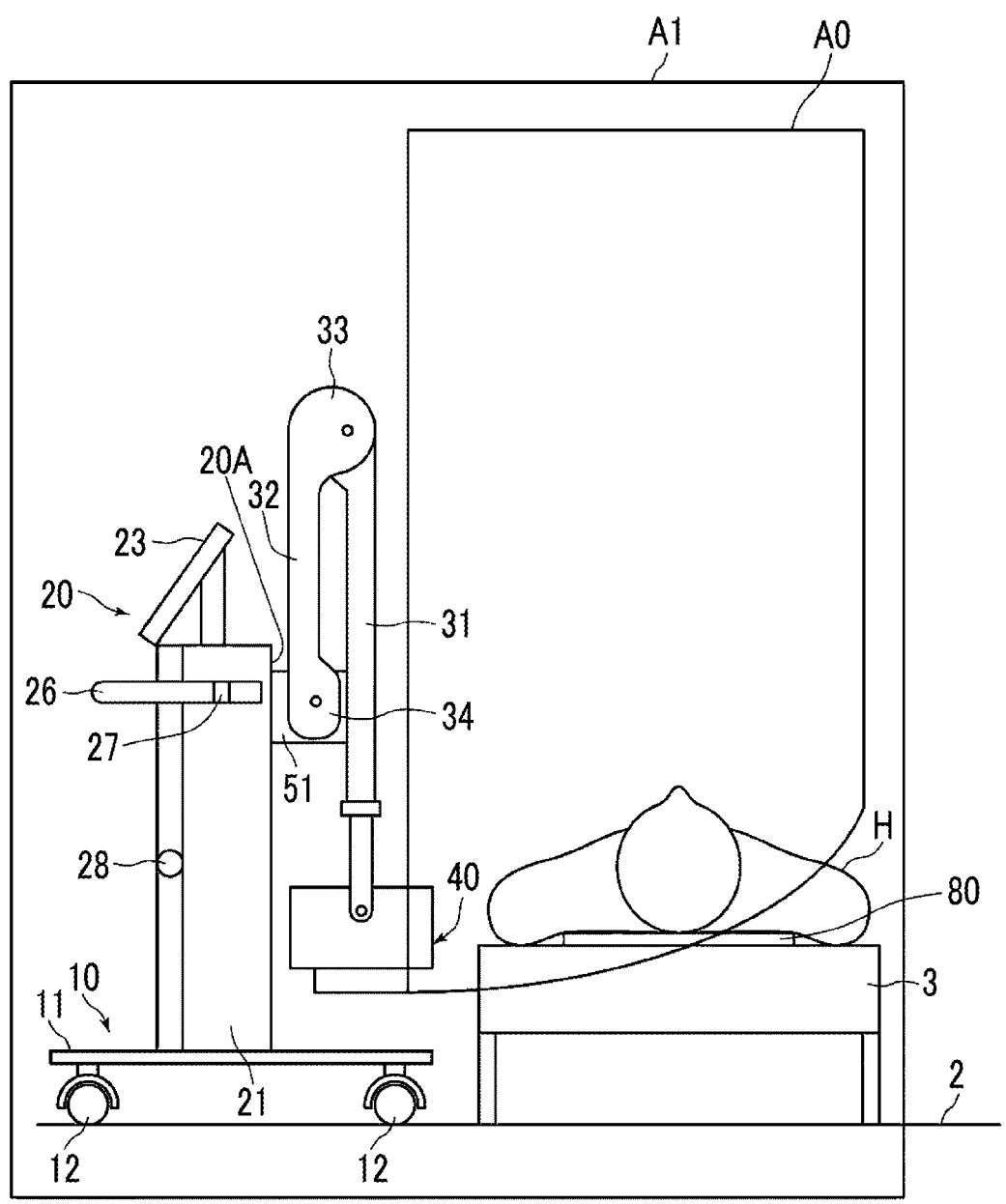
FIG. 12 is a diagram showing a composite side image.

The control unit 22 generates a composite side image where the calculated movable range A0 of the arm unit 30 and the radiation source unit 40 is superimposed on the side image A1, and displays the composite side image on the monitor 23. FIG. 12 is a diagram showing the composite side image.

In a case in which the subject H is to be imaged, a source image receptor distance (SID), which is a distance between the radiation source unit 40 and the surface of the radiation detector 80, is set as an imaging condition. For this reason, the control unit 22 may display the target position P1 of the radiation source unit 40, which is based on the SID, together with the side image A1 or the composite side image. A value, which is measured from the device-placement surface 2 in advance, may be input to the control unit 22 as the position of the surface of the radiation detector 80.

Since the composite side image where the movable range A0 of the radiation source unit 40 is combined with the side image A1 of the arm unit 30 viewed from the side is displayed on the monitor 23 as described above, an operator can recognize the movable range A0 of the radiation source unit 40. Accordingly, since the operator can move the radiation source unit 40 to a desired position while confirming the movable range A0 of the radiation source unit 40, it is possible to more reliably prevent the collision of the radiation source unit 40 with the bed 3 for the subject H and the like that is caused by the movement of the radiation source unit 40.

Figure 13:
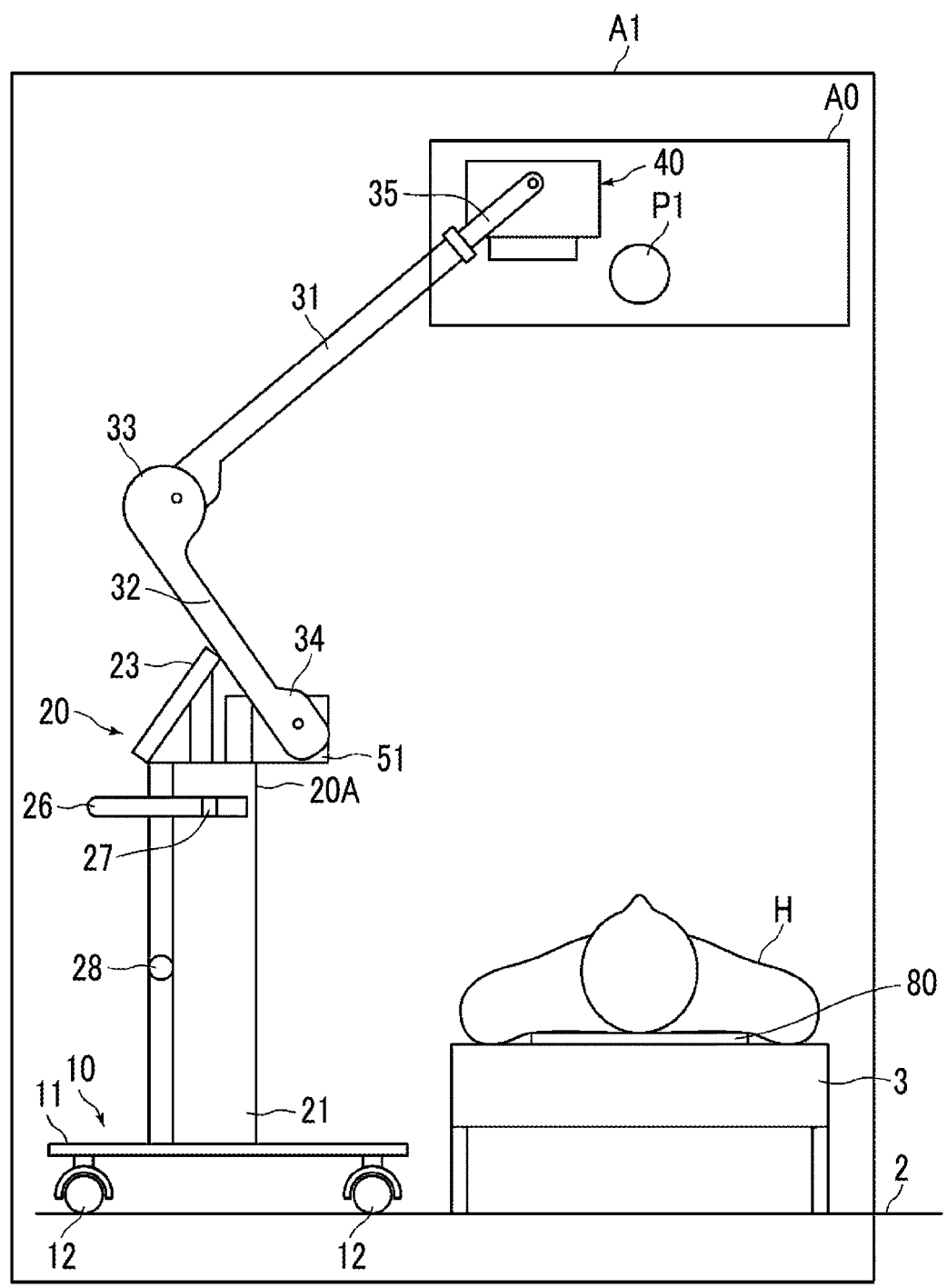
FIG. 13 is a diagram showing a composite side image on which a target position of the radiation source unit is superimposed.

Further, since the target position P1 of the radiation source unit 40 in a state in which the arm unit 30 is viewed from the side is displayed on the composite side image as shown in FIG. 13, the operator can easily move the radiation source unit 40 to the target position P1.

Here, various kinds of information required for the control of the device 1 is displayed on the monitor 23 as described above, but the control unit 22 may display the composite side image on the monitor 23 in a case in which the arms are operated and the change of at least one of the position of the second rotational moving portion 34 set by the raising/lowering mechanism 50, the first rotational movement angle, and the second rotational movement angle is detected by the sensor.

Further, a sensor for detecting the connection and non-connection of the connecting belt 36 may be provided, and the composite side image may be displayed on the monitor 23 in a case in which the connecting belt 36 is changed to a non-connection state from a connection state.

Incidentally, an operator works after moving to the side of the device 1 in a case in which the operator is to operate the arm unit 30. For this reason, the direction of the display surface of the monitor 23 is adapted to be capable of facing the side of the device 1. Accordingly, the operator can easily confirm the composite side image displayed on the monitor 23 while operating the arm unit 30. A sensor for detecting that the display surface of the monitor 23 faces the side may be provided, and the composite side image may be displayed on the monitor 23 by the control unit 22 in a case in which the sensor detects that the display surface of the monitor 23 faces the side. Further, the control unit 22 may be adapted to detect whether or not the radiation source unit 40 has been moved to the target position P1. In this case, the display of the monitor 23 may be switched to the display of various kinds of information, which is required for the control of the device 1, from the composite side image in a case in which it is detected that the radiation source unit 40 has been moved to the target position P1.

The regulating means of the invention is composed of the body unit 20 in the embodiment, but a mechanism for locking the rotational movement of the second rotational moving portion 34 may be provided as the regulating means in a case in which, for example, the arm unit 30 is positioned at a position other than the highest position by the raising/lowering mechanism 50.

Further, the body unit 20 composes the arm support unit according to the invention in the embodiment, but an arm support unit, which supports the arm unit 30, may be provided so as to stand on the leg unit 10 separately from the body unit 20.

Furthermore, in the embodiment, the second arm 32 can be rotationally moved in a case in which the arm unit 30 raised by the raising/lowering mechanism 50 is positioned at the highest position. However, a position where the second arm 32 can be rotationally moved is not limited to the highest position, and the second arm 32 may be rotationally moved at an arbitrary position close to the highest position.

Further, the rotational movement of the first arm 31 performed using the first rotational moving portion 33 is regulated in the embodiment by the connecting belt 36. However, other means, such as a lock mechanism, may be used.

Figure 14:
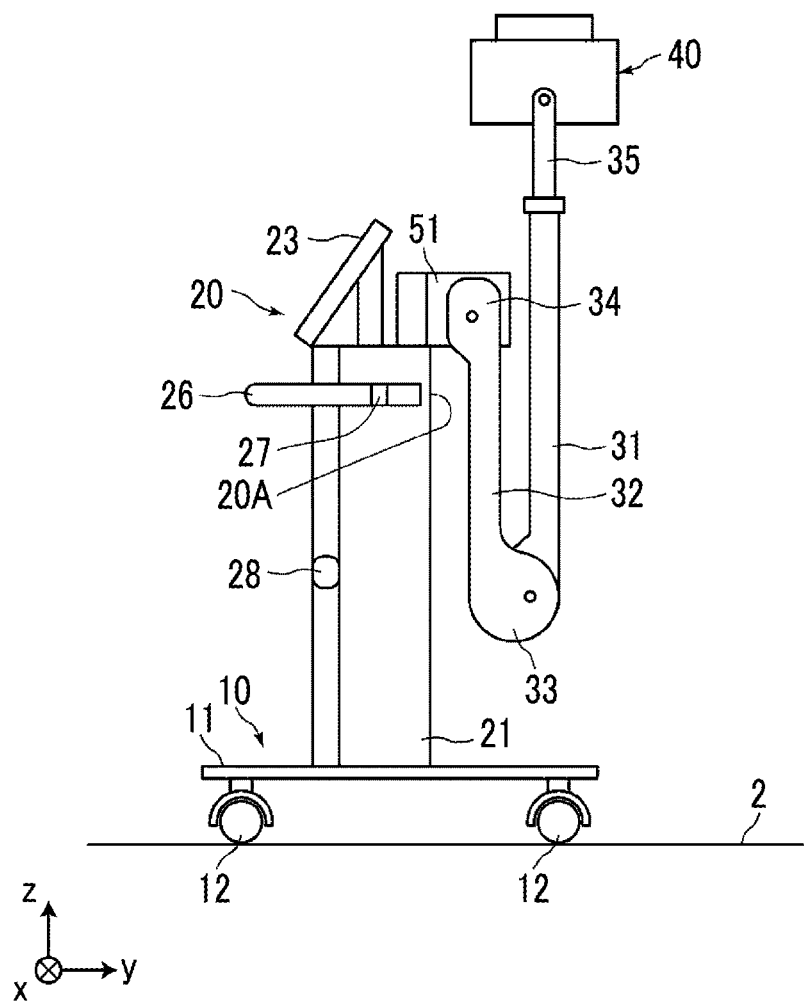
FIG. 14 is a diagram showing another structure of the arm unit.

Furthermore, the position of the arm unit 30 of which the second arm 32 is rotationally moved upward and the first arm 31 is rotationally moved downward, that is, the rotational movement position of the arm unit 30 shown in FIG. 1 is referred to as the initial rotational movement position in the embodiment. However, the rotational movement position of the arm unit 30 of which the second arm 32 is rotationally moved downward and the first arm 31 is rotationally moved upward as shown in FIG. 14 may be used as the initial rotational movement position of the arm unit 30. In this case, a lock mechanism, which regulates the clockwise rotational movement of the second arm 32 in FIG. 14 in a case in which the arm unit 30 is not positioned at the highest position and allows the second arm 32 to be rotationally moved in a case in which the arm unit 30 is positioned at the highest position, may be provided.

The effects of the embodiment of the invention will be described below.

In a case in which the initial rotational movement position is set to a position where the second arm 32 is rotationally moved upward relative to the main body 20, the arm unit 30 and the radiation source unit 40 are not moved to the subject, the bed, and the like through the regulation of the rotational movement of the second arm 32 toward the main body 20. For this reason, it is possible to prevent the collision of the arm unit 30 and the radiation source unit 40 with the subject, the bed, and the like that is caused by the movement of the arm unit and the radiation source unit toward the subject, the bed, and the like in a case in which the arm unit 30 is positioned at a position other than the first position.

Further, since the regulating means (comprising a surface 20A of the main body 20) releases the regulation of the rotational movement of the second arm 32 toward the main body 20 that is performed using the second rotational moving portion 34 in a case in which the arm unit 30 is positioned at the first position, the second arm 32 can be rotationally moved over the arm support unit comprising the main body 20. Accordingly, since the arm unit 30 and the radiation source unit 40 can be moved up through a position away from the subject, the bed, and the like, it is possible to more reliably prevent the collision of the arm unit 30 and the radiation source unit 40 with the subject, the bed, and the like.

Furthermore, since the regulating means comprising a surface 20A of the main body 20) is formed of the surface of the main body on which the arm unit 30 is supported, means for regulating the rotational movement of the second arm 30 does not need to be separately provided. Accordingly, the structure of the device can be simplified.

Further, since the first position is set to the highest position in the raising/lowering range in which the arm unit 30 is raised and lowered by the raising/lowering mechanism 50, the radiation source unit 40 can be moved in a direction where the radiation source unit 40 is lifted after the radiation source unit 40 is moved to the highest position. For this reason, it is possible to more reliably prevent the collision of the radiation source unit 40 with the subject, the bed, and the like that is caused by the movement of the radiation source unit 40.

Furthermore, since the arm support unit is composed of the body unit 20 that includes a computer for controlling the radiation source unit 40, a member having a function as the arm support unit does not need to be separately provided. Accordingly, the structure of the device can be simplified.

Further, since the arm unit 30 is revolvably supported by the main body 20, the radiation source unit 40 is more easily moved to a desired position.

Furthermore, the regulation of the revolution of the arm unit 30 is regulated in a case in which the arm unit 30 is positioned at a position other than the first position. Accordingly, even though the arm unit 30 is adapted to be revolvable, it is possible to prevent the collision of the radiation source unit 40 with the subject, the bed, and the like, which is caused by the movement of the radiation source unit 40 using revolution, in a case in which the arm unit 30 is positioned at a position other than the first position.

Further, since the rotational movement of the first rotational moving portion 33 is regulated, the movement of the first arm 30 and the radiation source unit 40 in a direction where the first arm 30 and the radiation source unit 40 are away from the second arm, which is caused by the rotational movement of the first arm 31 relative to the second arm 32, can be regulated. Accordingly, it is possible to more reliably prevent the collision of the first arm 31 and the radiation source unit 40 with the subject, the bed, and the like, which is caused by the movement of the first arm 31 and the radiation source unit 40, in a case in which the arm unit 30 is positioned at a position other than the first position.

Furthermore, since the movable range of the arm unit 30 and the radiation source unit 40, in a state in which the arm unit 30 is viewed from the side, is displayed on the monitor 23, an operator can recognize the movable range of the arm unit 30 and the radiation source unit 40. Accordingly, the operator can move the radiation source unit 40 to a desired position while confirming the movable range. Therefore, it is possible to more reliably prevent the collision of the arm unit and the radiation source unit with the subject, the bed, and the like that is caused by the movement of the arm unit 30 and the radiation source unit 40.

Further, since the target position of the radiation source unit 40, in a state in which the arm unit 30 is viewed from the side, is displayed on the monitor 23, the operator can easily move the radiation source unit 40 to the target position.

What is claimed is:

1. A radiation-irradiation device comprising:
a leg unit, including a base and wheels, that is capable of traveling on a device-placement surface;
a radiation source that irradiates a subject with radiation;
an arm unit, including a first arm and a second arm, that supports the radiation source;
a main body that stands on the leg unit and supports the arm unit; and
a raising/lowering mechanism, including a cylinder and a shaft, that raises and lowers the arm unit relative to the main body,
wherein the first arm of the arm unit is connected to the radiation source, and the arm unit further includes a first rotational moving portion that connects the first arm to the second arm so as to allow the first arm and second arm to be rotationally movable relative to each other, and a second rotational moving portion that connects the second arm to the raising/lowering mechanism so as to allow the second arm to be rotationally movable relative to the raising/lowering mechanism; and wherein a support surface of the main body on which the arm unit is supported regulates a rotational movement of the second arm from an initial rotational movement position, which is performed using the second rotational moving portion, in a case in which the arm unit is positioned at a position other than a first position, where the arm unit is raised or lowered by the raising/lowering mechanism.

2. The radiation-irradiation device according to claim 1, wherein the initial rotational movement position is a position where the second arm is rotationally moved upward, and the support surface of the main body regulates the rotational movement of the second arm toward the main body that is performed using the second rotational moving portion.

3. The radiation-irradiation device according to claim 2, wherein the support surface of the main body releases a regulation of the rotational movement of the second arm toward the main body that is performed using the second rotational moving portion in a case in which the arm unit is positioned at the first position.

4. The radiation-irradiation device according to claim 1, wherein the first position is a highest position in a raising/lowering range in which the arm unit is raised and lowered by the raising/lowering mechanism.

5. The radiation-irradiation device according to claim 1, wherein the main body includes a computer for controlling the radiation source.

6. The radiation-irradiation device according to claim 1, wherein the arm unit is revolvably supported by the main body.

7. The radiation-irradiation device according to claim 6, further comprising:

revolution regulating means, including a second cylinder, a second shaft and a keyway, for regulating a revolution of the arm unit in a case in which the arm unit is positioned at a position other than the first position.

8. The radiation-irradiation device according to claim 1, further comprising:

first-rotational-moving-portion regulating means, comprising a belt, for regulating a rotational movement of the first rotational moving portion.

9. The radiation-irradiation device according to claim 1, further comprising:

a display for displaying a movable range of the arm unit and the radiation source in a state in which the arm unit is viewed from a side.

10. The radiation-irradiation device according to claim 9, wherein the display displays a target position of the radiation source in a state in which the arm unit is viewed from a side.

* * * * *